(12) United States Patent
Fedick et al.

(10) Patent No.: US 12,390,811 B1
(45) Date of Patent: Aug. 19, 2025

(54) SAMPLING PLATFORM APPARATUS

(71) Applicants: The United States of America, as represented by the Secretary of the Navy, Arlington, VA (US); The Board of Trustees of Illinois State University, Normal, IL (US)

(72) Inventors: Patrick W. Fedick, Ridgecrest, CA (US); Hilary M. Brown, Chicago, IL (US); Christopher C. Mulligan, Bloomington, IL (US); Trevor J. McDaniel, Philadelphia, IL (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 332 days.

(21) Appl. No.: 18/121,336

(22) Filed: Mar. 14, 2023

Related U.S. Application Data

(63) Continuation-in-part of application No. 16/903,647, filed on Jun. 17, 2020, now Pat. No. 11,635,353.

(60) Provisional application No. 63/419,126, filed on Oct. 25, 2022.

(51) Int. Cl.
*B01L 3/00* (2006.01)

(52) U.S. Cl.
CPC .................... *B01L 3/5085* (2013.01)

(58) Field of Classification Search
CPC ............ B01L 3/5085; B01L 9/52; G01N 1/08
See application file for complete search history.

(56) References Cited

U.S. PATENT DOCUMENTS

| | | | | |
|---|---|---|---|---|
| 2,321,639 A | * | 6/1943 | Zarbo .................. | B01D 29/085 141/331 |
| 2,456,912 A | * | 12/1948 | Burrows ................ | B01D 35/28 229/4.5 |
| 2,633,410 A | * | 3/1953 | Beckley ............... | G01N 33/528 422/534 |
| 2,671,715 A | * | 3/1954 | Beckley ................ | G01N 33/68 422/534 |

(Continued)

FOREIGN PATENT DOCUMENTS

| | | | | |
|---|---|---|---|---|
| CN | 104392886 A | * | 3/2015 | .............. H01J 49/26 |
| EP | 762473 A2 | * | 12/1995 | |

OTHER PUBLICATIONS

Fedick et al. "A Low-Cost, Simplified Platform of Interchangeable, Ambient Ionization Sources for Rapid, Forensic Evidence Screening on Portable Mass Spectrometric Instrumentation," Instruments 2018, 2, 5 (Year: 2018).*

(Continued)

*Primary Examiner* — John Fitzgerald
(74) *Attorney, Agent, or Firm* — Naval Air Warfare Center Weapons Division; James M. Saunders

(57) ABSTRACT

The embodiments are directed to both sampling apparatuses and systems. Apparatus embodiments are directed to a sample collection apparatus having several receptacles configured to removably-hold sample collection devices. The sample collection devices are configured to hold a sample including solid media and analyte. System embodiments include the sample collection apparatus and several receptacles for removably-holding sample collection devices. The system embodiments also include additional components to perform analysis of the sample.

14 Claims, 10 Drawing Sheets

(56) References Cited

U.S. PATENT DOCUMENTS

| | | | | |
|---|---|---|---|---|
| 5,051,584 | A * | 9/1991 | Gray | H01J 49/105 |
| | | | | 250/281 |
| 5,078,189 | A * | 1/1992 | Ronsonet | B67C 11/02 |
| | | | | 141/331 |
| 5,480,072 | A * | 1/1996 | Ripley | B67C 11/02 |
| | | | | 141/334 |
| 5,793,039 | A * | 8/1998 | Oishi | H01J 49/067 |
| | | | | 250/288 |
| 6,803,568 | B2 * | 10/2004 | Bousse | H01J 49/0018 |
| | | | | 250/281 |
| 8,460,782 | B2 * | 6/2013 | Ivanov | C04B 35/16 |
| | | | | 428/297.4 |
| 9,346,045 | B2 * | 5/2016 | Blumentritt | G01F 23/02 |
| 10,545,073 | B2 * | 1/2020 | Pawliszyn | B01J 20/327 |
| 10,559,455 | B2 * | 2/2020 | Cooks | H05K 1/18 |
| 10,578,579 | B2 * | 3/2020 | Alonso Chamarro | |
| | | | | G01N 27/4161 |
| 11,635,353 | B2 * | 4/2023 | Fedick | G01N 33/24 |
| | | | | 73/863 |
| 11,667,992 | B2 * | 6/2023 | Dellis | C22C 5/04 |
| | | | | 420/467 |
| 2007/0084996 | A1 * | 4/2007 | Li | H01J 49/167 |
| | | | | 250/282 |
| 2011/0009774 | A1 * | 1/2011 | Calasso | A61B 5/150427 |
| | | | | 600/583 |
| 2011/0263005 | A1 * | 10/2011 | Chang | C12M 33/04 |
| | | | | 435/283.1 |
| 2013/0136672 | A1 * | 5/2013 | Blumentritt | B01L 3/0275 |
| | | | | 422/524 |
| 2013/0181010 | A1 * | 7/2013 | Ouyang | H01J 49/0009 |
| | | | | 222/209 |
| 2014/0001415 | A1 * | 1/2014 | Sheng | H01B 1/04 |
| | | | | 264/105 |
| 2014/0241956 | A1 * | 8/2014 | Page | G01N 1/4077 |
| | | | | 422/534 |
| 2017/0053788 | A1 * | 2/2017 | Cha | H01J 49/167 |
| 2017/0071710 | A1 * | 3/2017 | Deturmeny | A61C 17/02 |
| 2017/0105707 | A1 * | 4/2017 | Senior | A61B 10/0038 |
| 2017/0322179 | A1 * | 11/2017 | Alonso Chamarro | |
| | | | | G01N 27/4035 |

OTHER PUBLICATIONS

H. Brown, et al, Characterization and optimization of a rapid, automated 3D-printed cone spray ionization-mass spectrometry (3D-PCSI-MS) methodology, International Journal of Mass Spectrometry 474 (2022) 116781 (received Oct. 31, 2021, received revised form Dec. 20, 2021, available online Dec. 21, 2021 (9 pages).

* cited by examiner

SAMPLING PLATFORM APPARATUS

CROSS-REFERENCE TO RELATED APPLICATIONS

This application is a nonprovisional application claiming the benefit of U.S. provisional application No. 63/419,126, filed on Oct. 25, 2022, the contents of which are hereby expressly incorporated by reference in its entirety and which priority is claimed. This application is also a continuation-in-part application claiming the benefit of U.S. nonprovisional application Ser. No. 16/903,647 filed on Jun. 17, 2020 now U.S. Pat. No. 11,635,353, the contents of which are hereby expressly incorporated by reference in its entirety and which priority is claimed.

STATEMENT REGARDING FEDERALLY SPONSORED RESEARCH OR DEVELOPMENT

The invention described herein may be manufactured and used by or for the United States of America for governmental purposes without the payment of any royalties thereon or therefor. The subject matter of this invention is related to work conducted under Navy contract N689361920001.

FIELD

Embodiments generally relate to sampling platforms.

Figure 1:
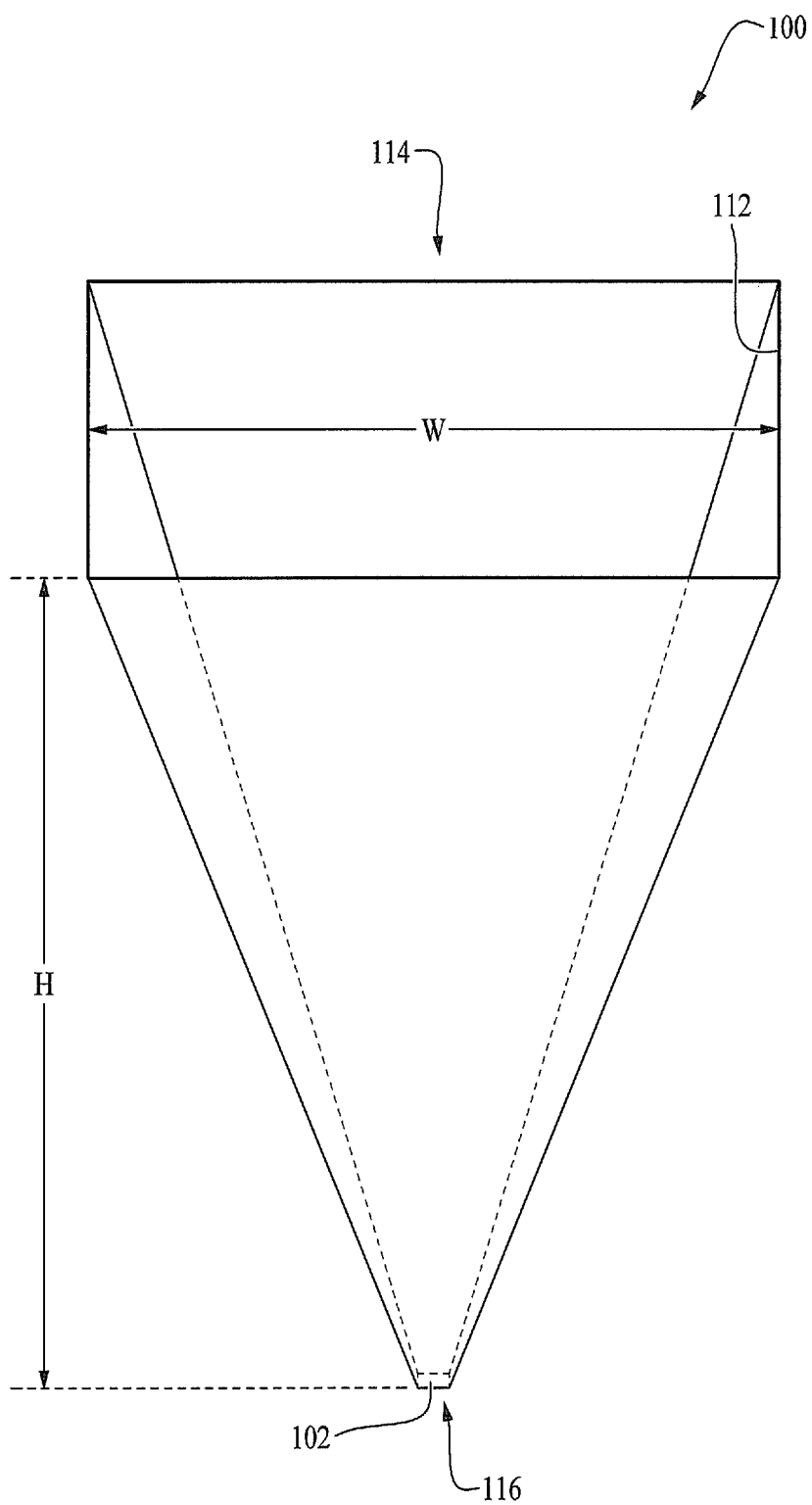
FIG. 1 illustrates an isometric view of a sample collection device, according to some embodiments.

It is to be understood that the foregoing general description and the following detailed description are exemplary and explanatory only and are not to be viewed as being restrictive, as claimed. Further advantages will be apparent after a review of the following detailed description of the disclosed embodiments, which are illustrated schematically in the accompanying drawings and in the appended claims.

DETAILED DESCRIPTION OF EMBODIMENTS

Embodiments may be understood more readily by reference in the following detailed description in connection with the accompanying figures. It is understood that embodiments are not limited to the specific devices, methods, conditions or parameters described and/or shown herein, and that the terminology used herein is for the purpose of describing particular embodiments by way of example only and is not intended to be limiting of the claimed embodiments.

The embodiments generally relate to sampling platforms and systems. In particular, the apparatus embodiments are configured to removably-hold sample collection devices. System embodiments include the apparatus in addition to components used in high throughput sample analysis. Some embodiments are sometimes referred to as a three-dimensional (3D)-printed cone spray ionization mass spectrometry (3D-PCSI-MS) sources. Other embodiments are simply referred to as apparatuses and systems. All embodiments have performed well in detecting and identifying analytes in bulk solids. In particular, working systems having shown increased throughout both in laboratory-based and in field conditions when components are coupled to a portable mass spectrometer.

Although the embodiments are described in considerable detail, including references to certain versions thereof, other versions are possible. Examples of other versions include varying component orientation or hosting embodiments on different platforms. Therefore, the spirit and scope of the appended claims should not be limited to the description of versions included herein.

Conventions, Parameters, and Terminology

At the outset, it is helpful to describe various conventions, parameters, and terminology associated with the embodiments.

Substantially

As used herein, unless otherwise specified, the term "substantially" refers to the complete, or nearly complete, extent or degree of an action, characteristic, property, state, structure, item, or result. As an arbitrary example, an object that is "substantially" surrounded would mean that the object is either completely surrounded or nearly completely surrounded. The exact allowable degree of deviation from absolute completeness may in some cases depend on the specific context. However, generally speaking, the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. As another arbitrary example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

About

The use of "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. As such, it is understood that the ranges provided herein include the stated range and any value or sub-range within the stated range. For example, a range from about 0.15 millimeters to about 0.25 millimeters should be interpreted to include not only the explicitly recited limits from about 0.15 millimeters to about 0.25 millimeters, but also to include individual values, such as 0.18 millimeters, 0.20 millimeters, 0.21 millimeters, etc., and sub-ranges, such as from about 0.17 millimeters to about 0.20 millimeters.

High-Voltage

The term "high-voltage" herein is in the kilovolts (kV) range. In particular, the ranges from about four kV to about seven kV are included. Voltage levels both above and below this range are possible and are based on application-specific conditions, including anticipated sample constituents.

Sample

The embodiments are used to perform analysis using mass spectrometers. The term "sample" is sometimes used. In the embodiments, the sample is a solid media that may or may not contain an analyte. Although the interest is to identify the analyte in the solid media, a person having ordinary skill in the art will recognize that the solid media may not contain analytes.

A person having ordinary skill in the art will recognize that the solid media device 100 can also hold a solid media that does not contain an analyte. Hence, at times, the solid media with or without an analyte can be referred to as a "sample," herein.

Apparatus and System Embodiments

In the accompanying drawings, like reference numbers indicate like elements. For all embodiments and figures, it is understood that the figures are not to scale and are depicted for ease of viewing. Reference characters 100, 200, 250, and 400 depict various embodiments, sometimes referred to as mechanisms, apparatus, devices, systems, and similar terminology. Several views are presented to depict some, though not all, of the possible orientations of the embodiments.

Figure 2A:
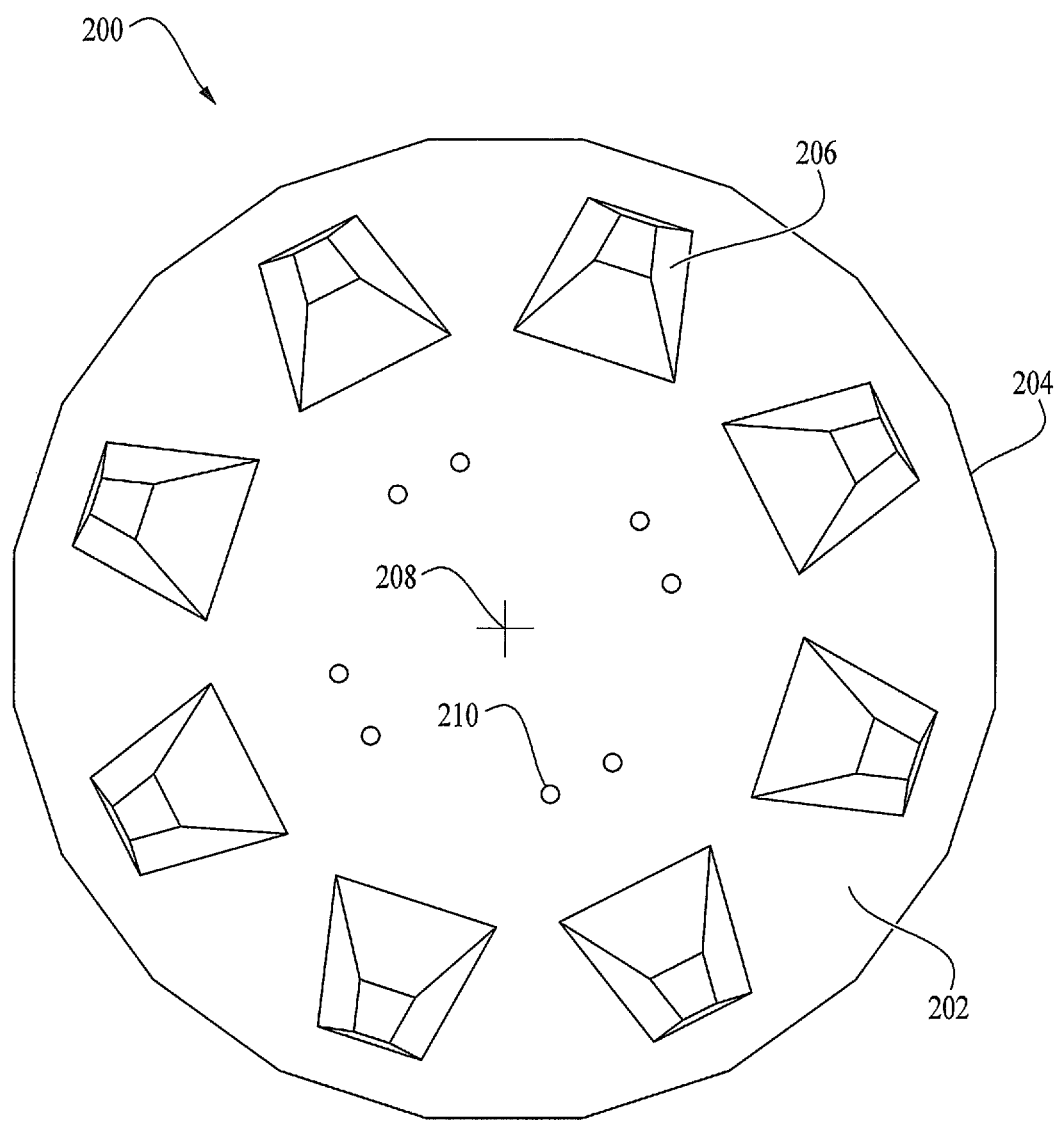
FIG. 2A illustrates a plan view of a sample collection apparatus having a plurality of receptacles, according to some embodiments.
Figure 2B:
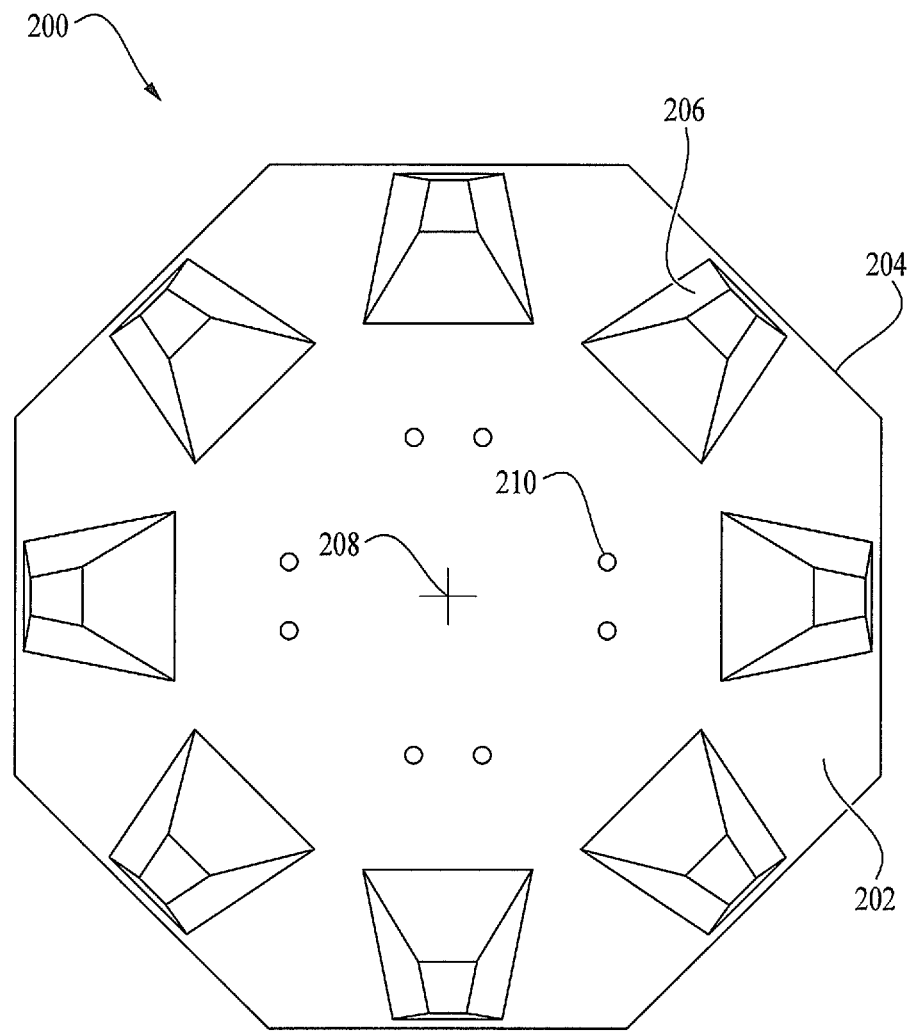
FIG. 2B illustrates a plan view of another sample collection apparatus having a plurality of receptacles, according to some embodiments.

FIG. 1 depicts an isometric view of a sample collection device 100. FIGS. 2A and 2B depict plan views of a sample collection apparatus 200. Although not exactly the same, the sample collection apparatuses 200 shown in FIGS. 2A and 2B are both disc-shaped and can be referred to as rotary.

Figure 9:
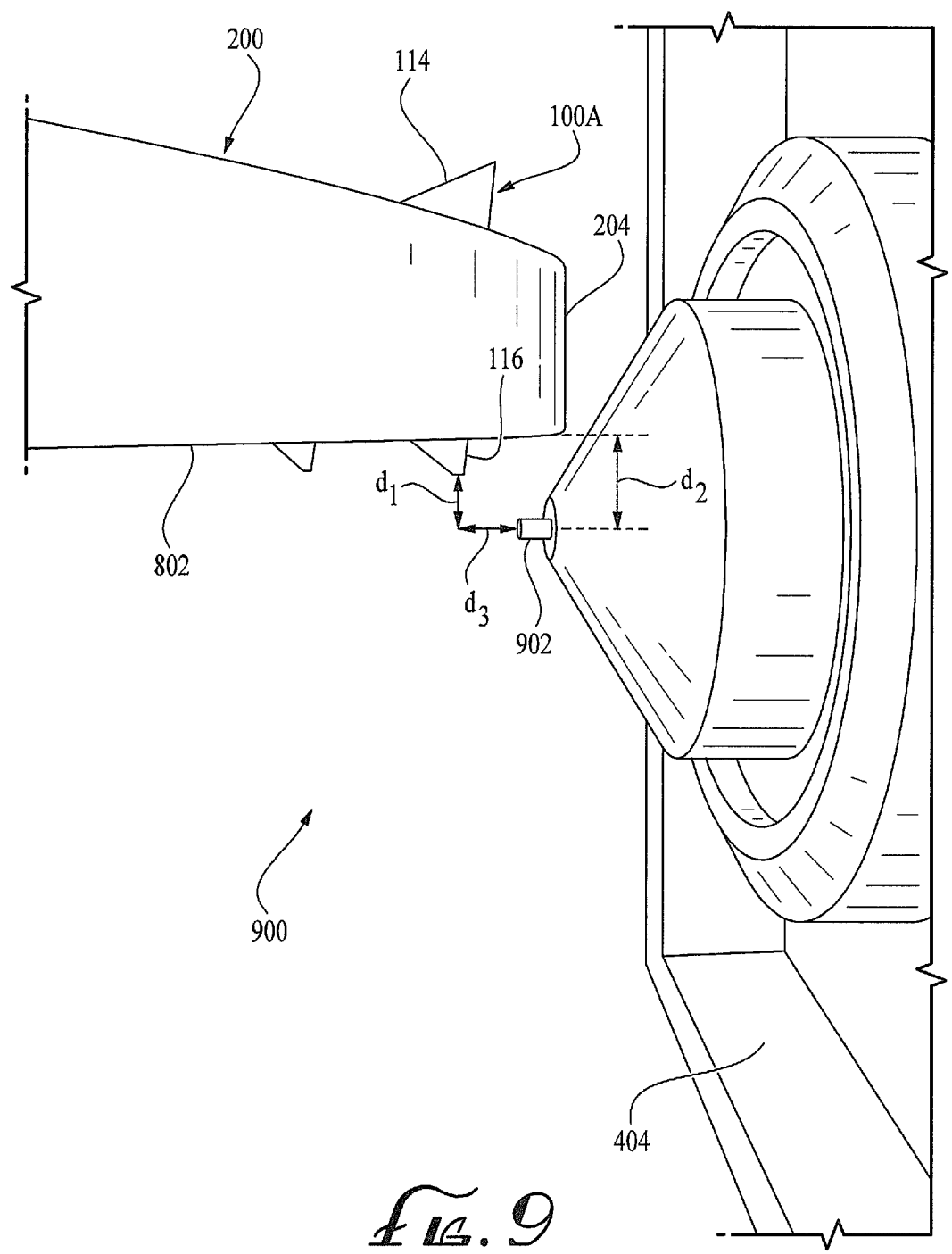
FIG. 9 illustrates a close-up side view of a portion of the sampling system in FIG. 4, illustrating the positioning and orientation of the sample collection apparatus and the distal end of the sample collection device in relation to the inlet of the mass spectrometer.

Referring to FIG. 2A a sample collection apparatus 200 is shown. The sample collection apparatus 200 can also be referred to as a sampling platform, a sample collection device holder, an autosampler, an apparatus, a platform, and similar variations. Referring to FIGS. 2A and 9 simultaneously, the sample collection apparatus 200 is a platform having a first side 202, a second side 802, and an outer edge 204. The first and second sides 202 and 802 can also be referred to as top and bottom sides, or upper and lower sides, respectively. A plurality of receptacles 206 extend through the platform 200 from the first side 202 to the second side 802. As such, the receptacles 206 perforate through both the first and second sides 202 and 802 and each receptacle in the plurality of receptacles can be referred to as an aperture or similar terminology without detracting from the merits or generalities of the embodiments.

Figure 3:
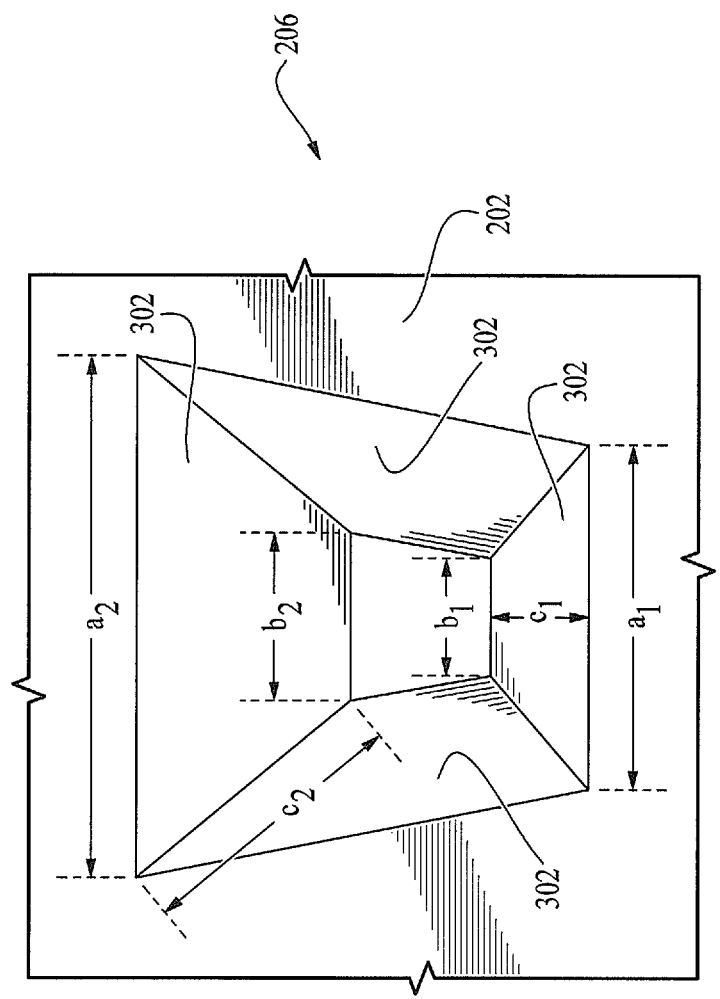
FIG. 3 illustrates a close-up view showing the geometry of a single receptacle, according to some embodiments.

Each receptacle in the plurality of receptacles 206 is configured to removably-hold a sample collection device 100 (shown in FIG. 1). Similarly, it can be equally said that each receptacle in the plurality of receptacles 206 is configured to receive or cradle the sample collection device 100. In practice, the number of sample collection devices 100 would match the number of receptacles in the plurality of receptacles 206. FIG. 3 shows a close-up view of a single receptacle in the plurality of receptacles 206. Importantly, it is evident that each receptacle in the plurality of receptacles 206 has inner walls 302 cooperating with the geometry of the sample collection device 100. Although four inner walls 302 are shown, it is understood that fewer or greater than four inner walls can be used without detracting from the merits or generalities of the embodiments. Additionally, the inner walls 302 shaped for quick alignment of the sample collection device 100. It is understood that the sample collection devices 100 fit in the receptacles 206 and held in place through either lost motion due to the geometry of the inner walls 302 or by friction fit with the inner walls.

As the shapes and dimensions of the sample collection device 100 can vary, so too can the shapes and dimensions of the receptacles 206. The receptacle 206 shown in FIG. 3 is typical of the receptacles in some embodiments. However, it is understood that dimensions and shapes in all embodiments for all components can be varied based on application-specific conditions. The receptacle 206 shown in FIG. 3 resembles a trapezoidal shape at both the first and second surfaces 202 and 802 of the sample collection apparatus 200. At opposing sides of the receptacle 206 at the first side 202, at least one dimension is two centimeters (shown as a1 in FIG. 3) and at least one dimension is three centimeters (shown as a2 in FIG. 3), with the respective sides parallel to each other. Similarly, at opposing sides of the receptacle 206 at the second side 902, at least one dimension is 0.6 centimeters (shown as b1 in FIG. 3) and at least one dimension is one centimeter (shown as b2 in FIG. 3), with the respective sides parallel to each other.

The inner wall nearest the outer edge 204 is vertical, i.e. perpendicular to the first and second sides 202 and 802, and has a dimension of 1.4 centimeters (shown as c1 in FIG. 3). The inner wall nearest the central longitudinal axis 208, i.e. farthest from the outer edge 204 is slanted at about 37 degrees from the first side 202 to second side 802 to accommodate proper fit for the sample collection devices 100 in the receptacles 206 for sample analysis. The intersection of at least two interior walls 302 forms creates an intersection distance of 2.5 centimeters (shown as c2 in FIG. 3) from the first side 202 to the second side 802. It should be noted that the dimensions and geometry shown is not to be construed as limiting, but is only for illustrative purposes.

Referring to FIG. 1, the sample collection device 100 has a proximal end 114 and a distal end 116. The distal end 116, which can also be referred to as a tip, has a hole 102 with a diameter range of about 0.15 millimeters to about 0.25 millimeters. The sample collection device 100 also includes a hollow interior 112 that forms a cavity, which can hold a solid media sample. The sample collection device 100 can be any hollow shape that terminates at a point and that can hold a solid media sample while allowing solvent extraction from the device during ambient ionization for mass spectrometer analysis. This diameter of the hole 102 has proven to be small enough to retain a solid media sample, but is large enough to allow solvent to exit during mass spectrometric analysis. The hole 102 allows for analysis via ambient ionization after the solvent has passed through the solid media and solvent extraction of analyte has occurred.

The sample collection device 100 also has a height and a width, shown as h and w, respectively, in FIG. 1. The height h and width w can be any height and width that is large enough to hold a solid media sample, but small enough to remain portable while using the least amount of material as possible. The height h is defined as the vertical distance from the hole 102 at the distal end 116 of the sample collection device 100 to the proximal end 114. The width w is defined as the furthest distance from the inner side of a wall to the opposite inner side of a wall of the sample collection device 100. In an embodiment, the sample collection device 100 may have a height h and a width w ranging from about 12.5 millimeters to about 40 millimeters.

The sample collection device 100 also has a thickness that is large enough to hold a solid media sample, but small enough to retain the device's original shape while using the least amount of material as possible. The sample collection device's 100 thickness is defined as the distance from the inner side of a wall to the outer side of a wall. In an embodiment, the sample collection device 100 has a thickness ranging from about 0.6 millimeters to about 3 millimeters. The sample collection device 100 can be made using any known methods to produce a conductive polymer device, including 3D printing. Once produced, the sample collection device 100 can be used immediately to collect samples for mass spectrometer analysis.

The sample collection device 100 is made of a conductive polymer. The conductive polymer includes a mixture of carbon nanotubes and a polymer. Alternatives to the carbon nanotubes include metal-infused polymers such as, for example, copper and conductive resins. The polymer may be any polymer that can be subjected to a voltage and is immiscible with the extraction and spray solvent. For example, the polymer may be polyethylene terephthalate, acrylonitrile butadiene styrene, polylactic acid, polyetherketoneketone, polyether ether ketone, polycarbonate, polyphenylene sulfide, polyvinylidene fluoride, and combinations thereof. The carbon nanotubes may be any carbon nanotubes that conduct electricity. An example of the carbon nanotubes is multi-wall carbon nanotubes.

The platform 200 has a central longitudinal axis 208. The plurality of receptacles 206 are axially-spaced at equal distance about the central longitudinal axis 208. The platform 200 is, in several embodiments, generally a disc and is sometimes referred to as disc-shaped, rotary-shaped, or substantially-circular. The platform 200 can also be referred to as rotary, a rotary disc, or rotary platform. It is evident when viewing FIGS. 2A, 2B, and 4 through 8 that the sample collection apparatus 200 is polygonal in plan view, i.e. is a polygonal shape, while still maintaining a rotary or substantially-circular, disc shape. FIG. 2A depicts the outer edge 204 as having twenty sides. Whereas, FIGS. 2B and 4 through 8 show the platform 200 having its outer edge 204 defined by eight sides, i.e. being octagonal in plan view or having an octagonal shape. In all instances, it is evident that all of the above shapes are applicable without detracting from the merits or generalities of the embodiments. Likewise, the sample collection apparatus 200 is not specifically limited to the number of sides forming its outer edge 204.

The rotary, disc-shaped platforms in FIGS. 2A and 2B are about 16 centimeters in diameter. The distance between diametrically-opposed receptacles 206, i.e. receptacles 180 degrees apart is about 10 centimeters. The platform 200 thickness, measured parallel to the central longitudinal axis 208 and perpendicular to the first and second sides 202 and 802 is about 1.4 to about 1.5 centimeters, however it can range from about one centimeter to about ten centimeters, depending on application-specific conditions. It is understood that the dimensions can be varied to accommodate larger or smaller platforms 200, as well as different receptacle 206 geometries and dimensions.

Figure 2C:
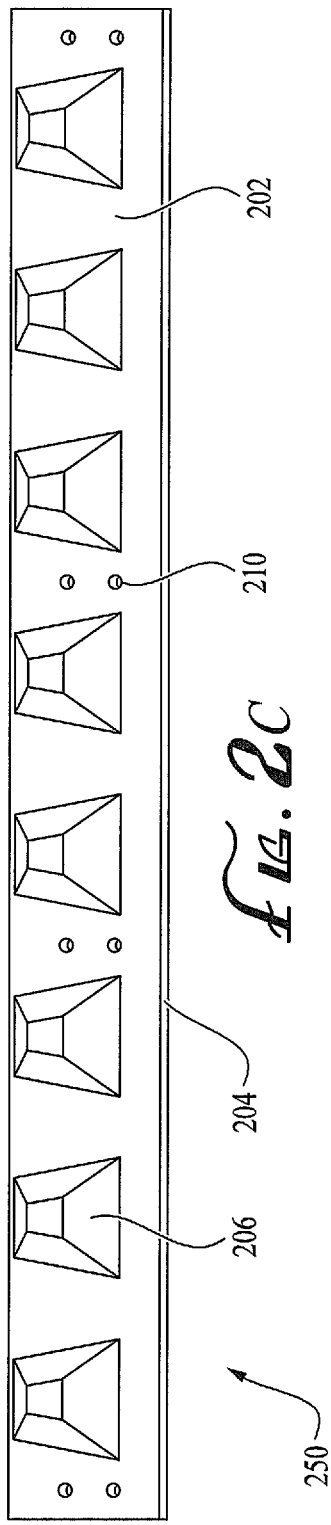
FIG. 2C illustrates a plan view of yet another sample collection apparatus having a plurality of receptacles, according to some embodiments.

FIG. 2C illustrates another embodiment, depicted with reference character 250, of the sample collection apparatus shown in a linear rail orientation. The sample collection apparatus 250 in FIG. 2C is a platform and is rectangular in shape and also has a plurality of receptacles 206 through both sides of the platform. As before, the first side is depicted with reference character 202. The second side is not viewable in FIG. 2C, but a person having ordinary skill in the art will recognize that the linear rail orientation platform 250 includes the second side. The outer edge 204 forms the rectangular shape of the sample collection apparatus 250 in FIG. 2C. As before, the receptacles 206 in the sample collection apparatus 250 in FIG. 2C are configured to accommodate sample collection devices 100, both in number and the previously discussed dimensions and geometries. The sample collection apparatus 250 in FIG. 2C has thickness is about 1.4 to about 1.5 centimeters, however it can range from about one centimeter to about ten centimeters, depending on application-specific conditions.

In some embodiments, the number of receptacles in the plurality of receptacles 206 is a range of about four to about twelve receptacles and, hence, the number of sample collection devices 100 would also be a range of about four to about twelve devices. In other embodiments, the range can be greater such as, for example, three to twenty receptacles 206 and sample collection devices 100. As such, any number of receptacles 206 and sample collection devices 100 can be used, based on the dimensions of the sample collection apparatuses 200 and 250, without detracting from the merits or generalities of the embodiments.

In the disc-shaped, rotary-shaped, or substantially-circular embodiments in FIGS. 2A, 2B, and 4 through 8, the axial spacing is a range of about 30 degrees to about 90 degrees. The plurality of receptacles 206 in the linear rail orientation (250 in FIG. 2C) are in a series arrangement with equal spacing between adjacent receptacles. The figures, for ease of viewing, depict the plurality of receptacles 206 has being eight receptacles, but it is understood that any number can be used based on application-specific conditions. For instance, in other disc-shaped, rotary-shaped, or substantially-circular embodiments, the axial spacing can be a range of about 18 degrees to about 120 degrees, based on the dimensions of the sample collection device 200.

The sample collection device 100 is hollow and is configured to hold a solid media containing an analyte. In some embodiments, the sample collection device 100 is a hollow multi-faced pyramid. In other embodiments, the sample collection device is a hollow cylindrical cone. The polymer of the sample collection device 100 is selected from the group consisting of polyethylene terephthalate, acrylonitrile butadiene styrene, polylactic acid, polyetherketoneketone, polyether ether ketone, polycarbonate, polyphenylene sulfide, polyvinylidene fluoride, and combinations thereof. The solid media is selected from the group consisting of soil, sand, sediment, waste, pure analytes, and combinations thereof. Toxicology samples and analysis can be included in the embodiments, based on application-specific conditions. The analyte is selected from the group consisting of perfluoroalkyl substances, polyfluoroalkyl substances, energetics, chemical warfare agent simulants, drugs of abuse, pesticides, and combinations thereof. Any perfluoroalkyl substances, polyfluoroalkyl substances, energetics, chemical warfare agent simulant, drugs of abuse, or pesticides known to those skilled in the art may be used as the analyte depending on the purpose of evaluating the solid media.

Some specific examples of perfluoroalkyl substances include perfluorodecanoic acid, heptafluorobutyric acid, perfluorotridecanoic acid, perfluoroheptanoic acid, perfluorooctane-sulfonic acid, perfluoroundecanoic acid, perfluorooctance-sulfonamide, tridecafluorooctane-1-sulphonic acid, perfluorooctanoic acid, perfluorononanoic acid, tricosafluorododecanoic acid, or combinations thereof.

The sample collection apparatuses discussed—both rotary or disc-shaped 200 and rectangular or linear rail 250 versions, are made from non-conductive, chemically-inert plastics. Suitable materials for the sample collection apparatuses 200 and 250 include plastics such as polylactic acid (PLA), polyethylene terephthalate glycol (PETG), and acrylonitrile butadiene styrene (ABS). Fabrication techniques of the sample collection apparatuses 200 and 250 include 3-D printing and machining techniques such as computerized numerical control (CNC) and injection molding.

Samples in the sample collection devices 100 are not shown for ease of viewing, especially due to the vast differences in substances that can be analyzed. Samples, i.e. solid media for analysis, can consist of the analyte in its solid form (powders, pressed powders, tablets, crystals, etc.) or an analyte within, or upon, a solid matrix (i.e. per—and polyfluoroalkyl substances (PFAS) in soil, sediment, or solid waste). The solid samples can be scooped or shoveled into the sample collection device.

Figure 4:
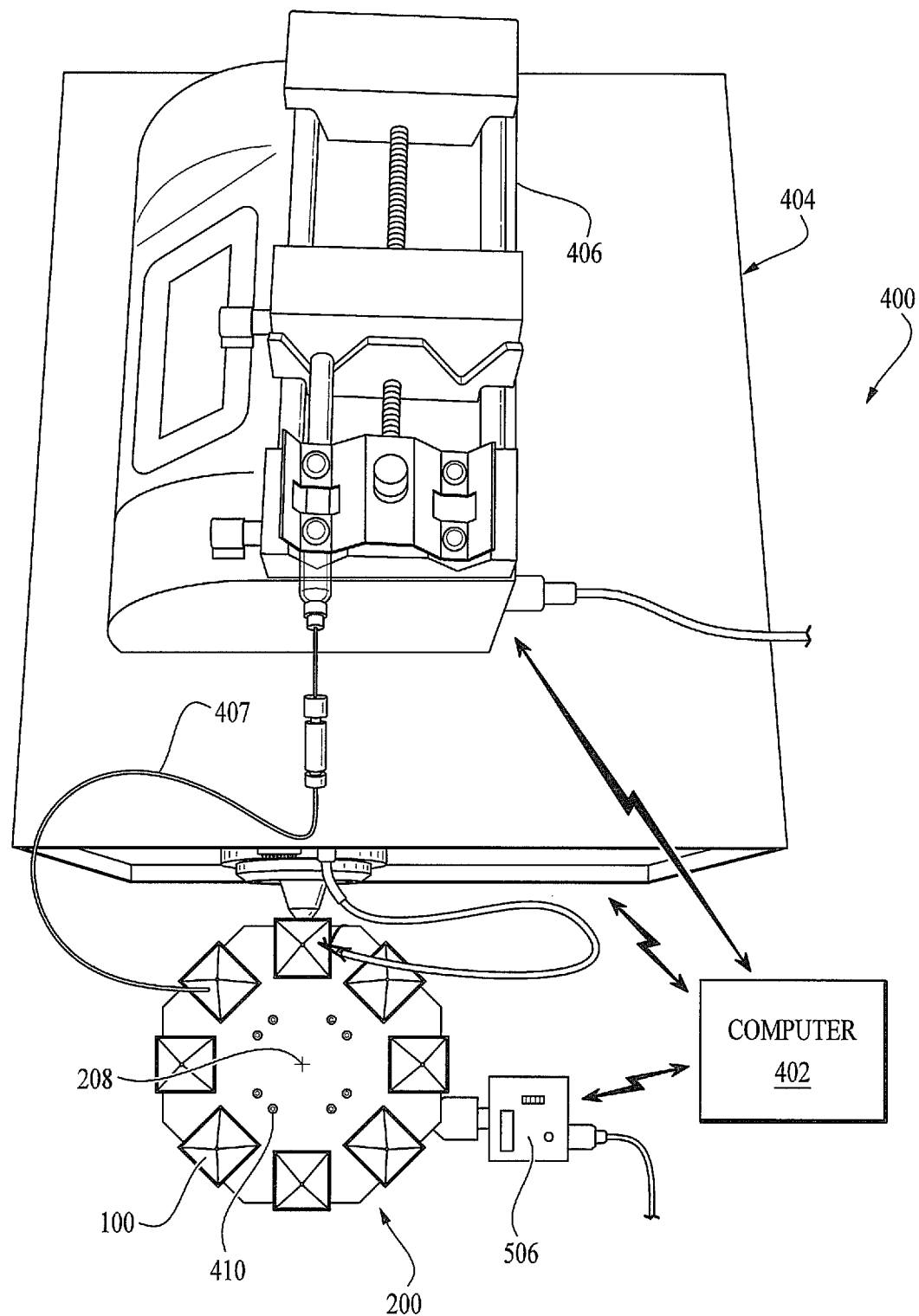
FIG. 4 illustrates a plan view of a sampling system, according to some embodiments.
Figure 5:
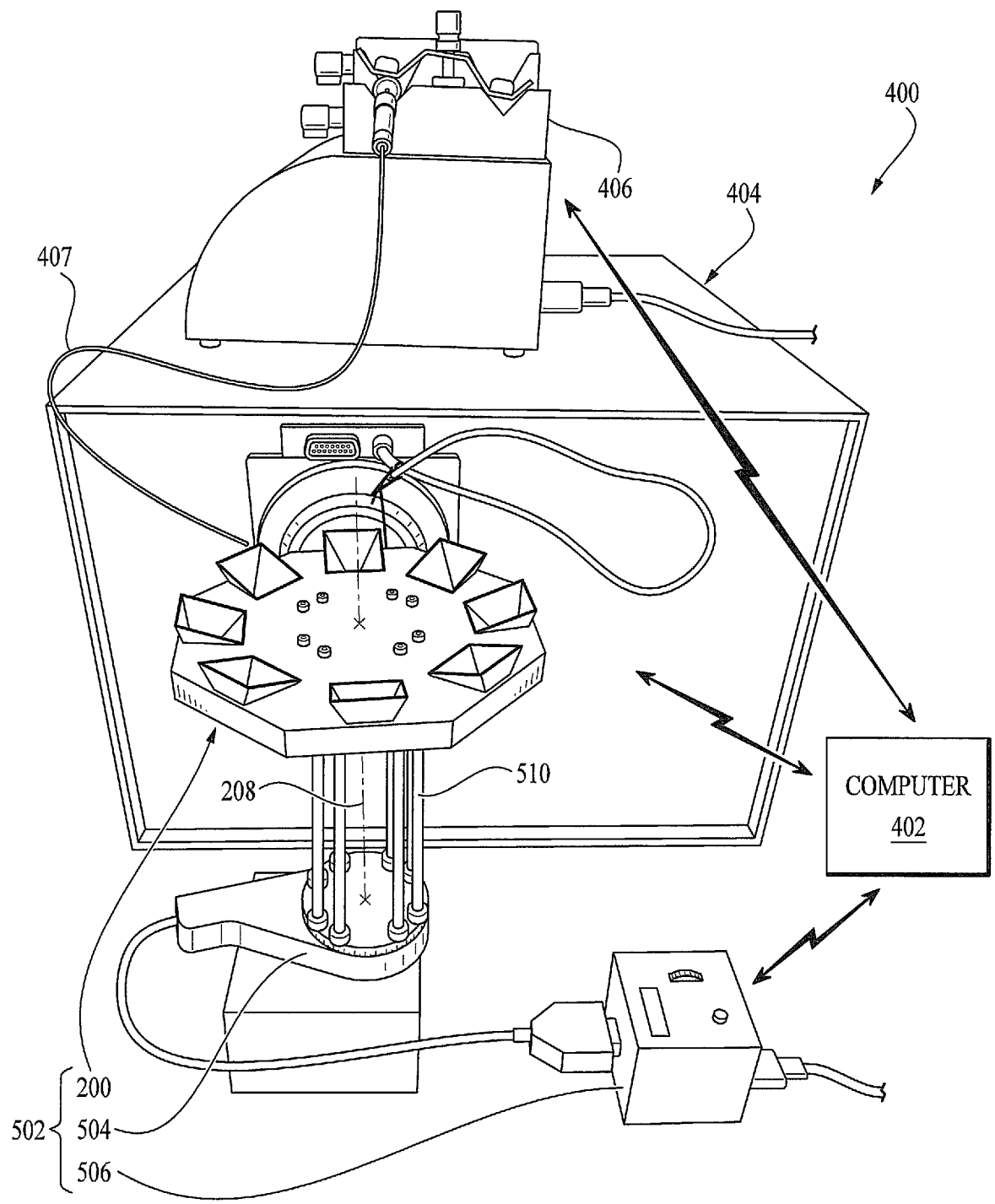
FIG. 5 illustrates an isometric view of the sampling system in FIG. 4.

The system embodiments in FIGS. 4 through 9 may refer to the platform 200 as rotary disc or rotary platform. FIG. 4 illustrates a plan view of a working sampling system 400. FIG. 5 illustrates an isometric view of the system 400. The system 400 includes a motorized platform 502, which is best viewed in its entirety in FIG. 5. The motorized platform 502 includes a rotary disc 200, an electric motor 504, and controller 506. The electric motor 504 can also referred to as a motor. A person having ordinary skill in the art will recognize that the apparatuses (i.e. platforms 200 from FIGS. 2A and 2B) can be used interchangeably in the system 400 for the rotary disc without detracting from the merits or generalities of the embodiments. The motorized platform 502 is configured with the rotary disc 200 electromechanically-coupled to the electric motor 504 and controller 506. A person having ordinary skill in the art will recognize that the electric motor 504 and controller 506 can also be a single component, such as a servo-controller or separate components without detracting from the merits or generalities of the embodiments. It is also understood that, should a user wish to do so, the rotary disc 200 could be manually-rotated into specific positions that would allow for analyses, without including or using the electric motor 504 and controller 506.

The rotary disc 200, has a first side 202, a second side 802, an outer edge 204, and a central longitudinal axis 208. Mounting holes 210 are shown in FIGS. 2A and 2B, as well in FIG. 2C. The mounting holes 210 are also used in the system 400 embodiments shown in FIGS. 4, 5, 6, and 8. The mounting holes 210 are used to secure the rotary disc 200 to the electric motor 504. The motor 504 used is a rotation stage platform and was the base for the rotary disc 200 for automated control. Eight mini-series adaptors with external M4 threads and internal M3 threads were inserted at equidistant positions in the mounting holes 210. Two mini-series optical posts, each having with a six millimeters diameter and a length of 75 millimeters, were screwed into each mini-series adapter to create eight posts 510 each about 150 millimeters tall. The posts 510, which can also be referred to as mounting posts or rods, attach the rotary disc 200 to the electric motor 504. M3 screws 410, each having a length of thirty millimeters, were threaded through the mounting holes 210 from the first side 202 to attach the rotary disc 200 to the posts 510 that were inserted through the mounting holes on the second side 802. The rotary disc 200, posts 510, and screws used for secure attachment can be adjusted based on the environment, including height requirements of the mass spectrometer 504 being used. It is understood that a different number of posts 510 can be used and that the sizes can be varied based on user discretion. Additionally, it is understood that various lifts, tables, stands, bars, and clamps are used for height and placement purposes based on environment conditions, i.e. laboratory versus use.

The system includes a computer 402 used for communicating with components. Communication links throughout the system 400 can be wireless data links, hard-wired, or a combination of the two depending on component capabilities. The communication links are generically shown by jagged lines with arrows. The computer 402 is in communication with the motorized platform 502 and, in particular, the controller 506 to provide instructions to the controller. The controller 506 is configured to prompt the electric motor 504 to actuate, i.e. engage, based on received computer instructions. It should be noted that the computer 402 can be referred to as a non-transitory electronic processor readable medium. Based on this, the computer instructions are electronic processor executable instructions that, when executed by the processor, causes the processor to perform the processes described herein. It is understood that the computer 402 can be a desktop, laptop, tablet, or handheld computer such as, for example, a mobile phone, without detracting from the merits or generalities of the embodiments. It is also understood that a user can start the sample analysis using the system 400 by selecting an icon or executable file on the computer 402 such as, for example running a computer program. Additionally, it is also understood that the computer 402 includes a display screen for user viewing.

The computer 402 is also in communication with a mass spectrometer 404, via a dedicated internal mass spectrometer computer (not visible for ease of viewing and due to it being internal). The mass spectrometer 404 has a sampling inlet 902, which is illustrated in a close-up view in FIG. 9. The sampling inlet 902, is sometimes referred to as a mass spectrometer inlet or simply as the inlet, provides a vacuum. The system 400 includes a syringe pump 406, having a dedicated internal syringe pump computer (not visible for ease of viewing and due to it being internal). The computer 402 and syringe pump 406, via the dedicated internal syringe pump computer, are configured to communicate with each other. Both the dedicated internal syringe pump computer associated with the syringe pump 406 and the dedicated internal mass spectrometer computer associated with the mass spectrometer 404 can also be referred to as a non-transitory electronic processor readable mediums. Based on these aspects, the mass spectrometer 404 and the syringe pump 406 can communicate with each other in some embodiments via their dedicated internal computers, i.e. the dedicated internal syringe pump computer and the dedicated internal mass spectrometer computer. All communication in the system 400 both to and from the computer 402, both to and from the dedicated internal syringe pump computer, and both to and from the dedicated internal mass spectrometer computer can be referred to as electrical communication or as signal communication, which is strictly non-transitory signal communication.

The mass spectrometer 404 has an internal power source (not visible for ease of viewing and due to it being internal). The power source is configured to apply a high voltage as discussed below and can be referred to as a voltage source or high voltage source. All components in the system 400 such as, for example, the computer 402, the mass spectrometer 404, syringe pump 406, the electric motor 504, and controller 506, can be configured to access multiple power sources, including alternating current (AC) or direct current (DC), solar, wind, and generator power, with any required adaptor or transform techniques included. Additionally, mechanically-driven systems are included such as, for example, internal combustion engines, two and four-cycle engines, and tractor power take off shafts in place of the electric motor 504, without detracting from the merits or generalities of the embodiments.

Figure 8:
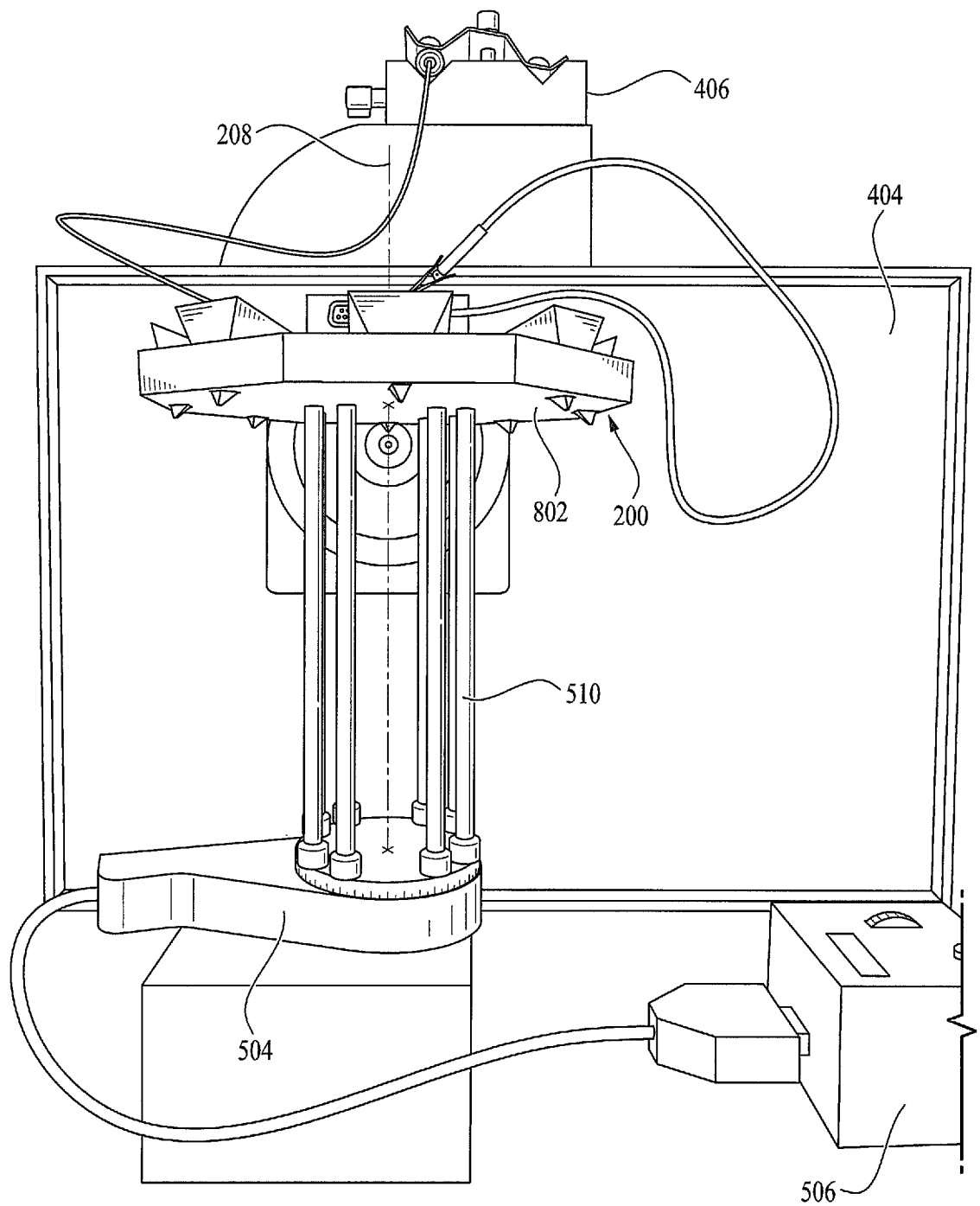
FIG. 8 illustrates an isometric view of the sampling system in FIG. 4 including a view of the underside of the sample collection apparatus.

Referring to FIGS. 4, 5, and 8, the plurality of receptacles 206 extend through the rotary disc 200 from the first side 202 to the second side 802, and are axially-spaced at equal distance about the central longitudinal axis 208. It is evident that the first side 202 can also be referred to as the top side or top surface. Similarly, the second side 802 can also be referred to as the bottom side or bottom surface. The plurality of receptacles 206 are apertures through the rotary disc 200. Each receptacle in the plurality of receptacles 206 is configured to removably-hold a sample collection device 100, sometimes referred to as a corresponding sample collection device.

Figure 6:
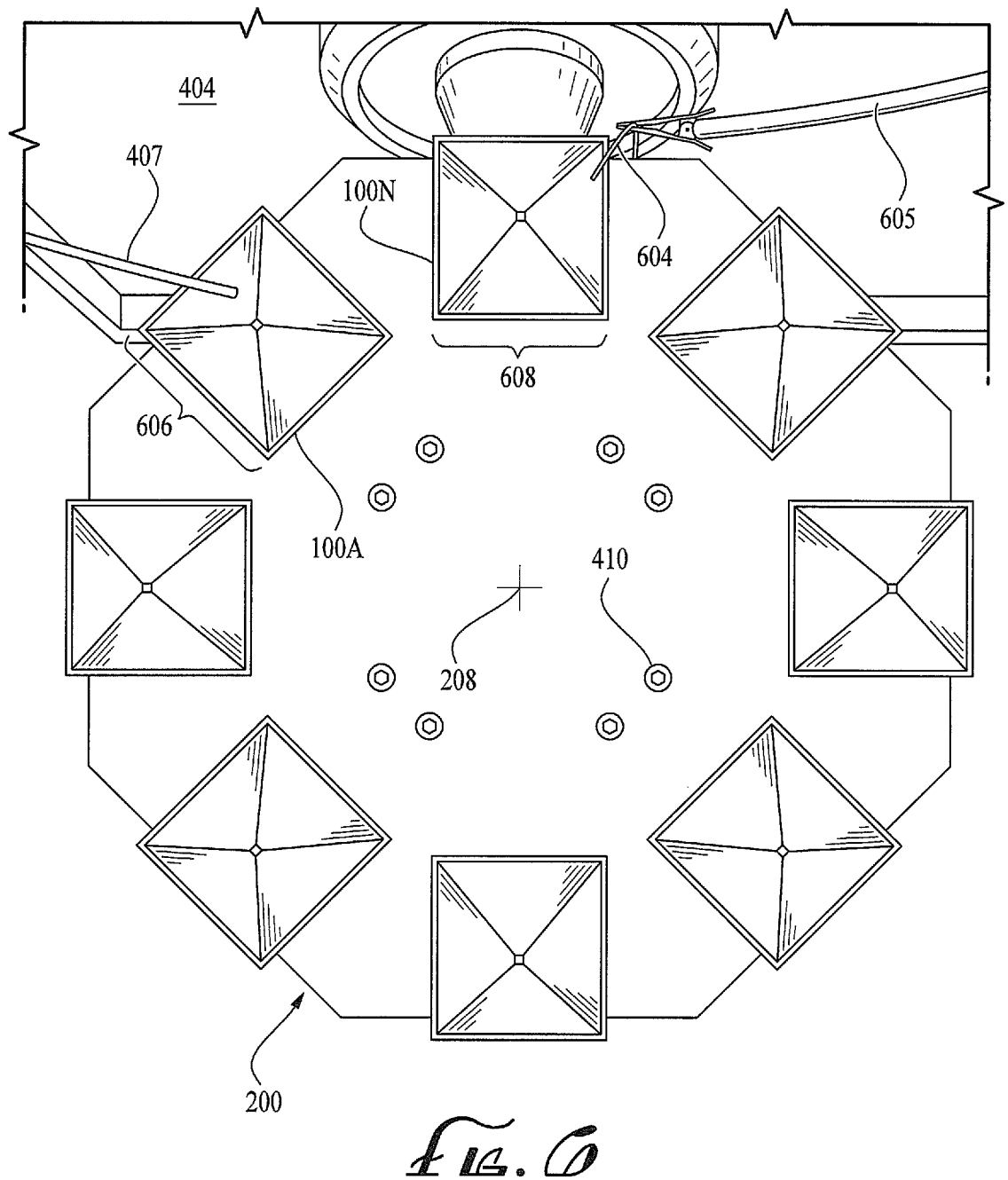
FIG. 6 illustrates a close-up plan view of the sample collection device in the sampling system in FIG. 4, including a solvent fill position and a high voltage application position.
Figure 7:
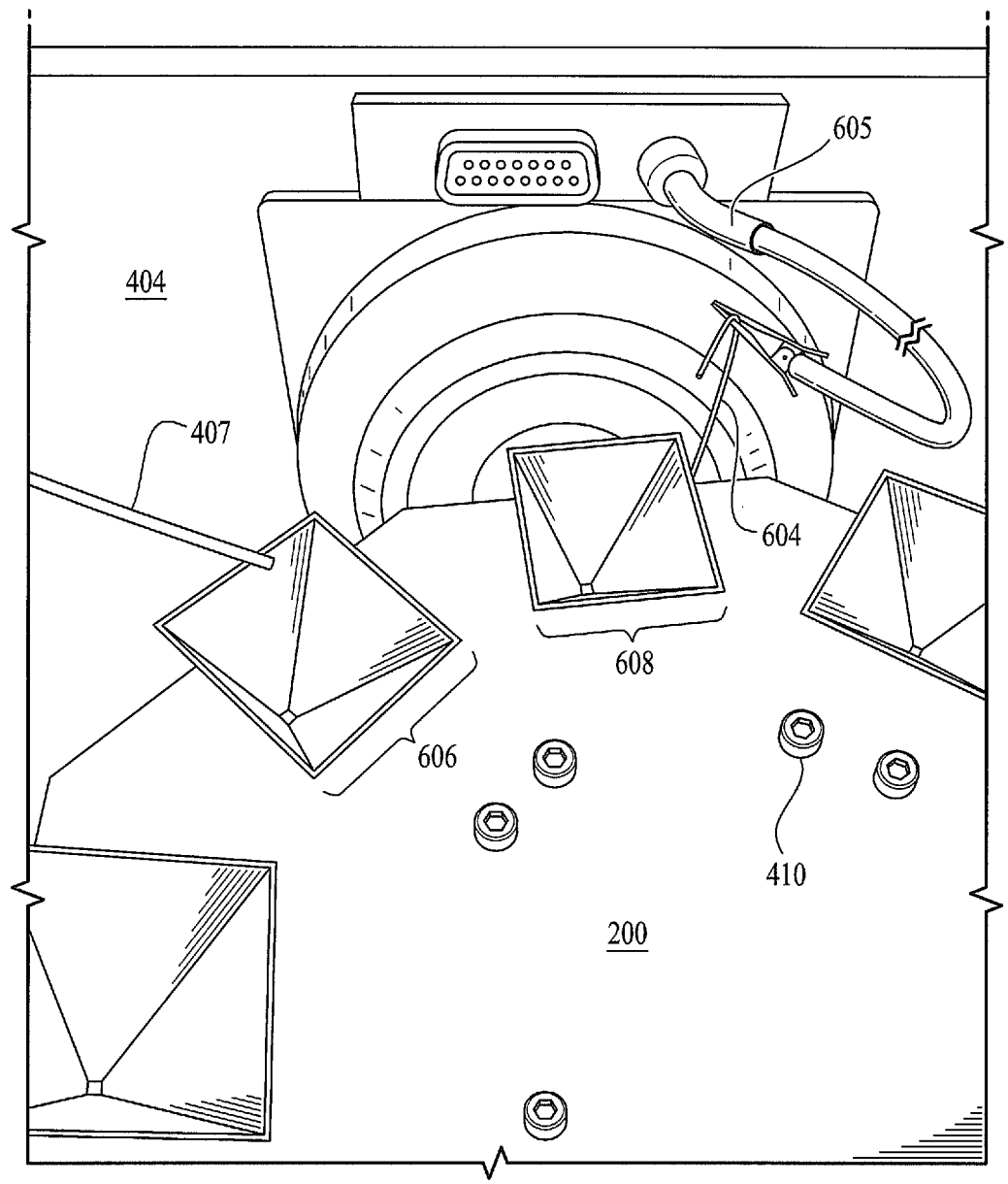
FIG. 7 illustrates a close-up isometric view of a portion of the sampling system in FIG. 4, including a close-up view of the solvent fill position and the high voltage application position, and the location of a connection to an internal power source in a mass spectrometer.

As shown in FIGS. 4, 5, and the close-up view in FIG. 6, each receptacle in the plurality of receptacles 206 has a dedicated sample collection device 100, which in the system environment 400, can be referred to as a corresponding sample collection device. The syringe pump 406 is in fluid communication with the each of the sample collection devices 100, i.e. in fluid communication with each corresponding sample collection device 100, based on the rotation and advancement of the rotary disc 200. A syringe hose 407 is connected to the syringe pump 406, providing the fluid communication from the syringe pump to the sample collection device 100 and enabling solvent to be deposited on the sample in the sample collection device.

Similarly, FIG. 6 depicts a wire 604 in contact with the proximal end 114 of the sample collection device. The wire 604 is electrically-connected to the mass spectrometer's 404 internal power source by an electrical cable 605. Thus, due to the sample collection device 100 being conductive and its proximal end 114 being in contact with the wire 604, the sample collection device is electrically-connected to the power source. By virtue of this connection, the mass spectrometer 404, through its power source, is configured to apply a high voltage to the sample collection device 100 in contact with the wire 604. One having ordinary skill in the art will understand that alternatives to the wire 604 exist to create a path for high voltage application. Some alternatives include providing a conductive portion such as, for example, using ball bearings embedded into the rotary disc 200 or having a conductive plastic portion or conductive plastic polymer portion in the rotary disc that contacts the sample collection device 100.

Referring to FIGS. 6 and 9, the sample in the sample collection device 100 to the left of the inlet 902 is defined as a solvent fill position 606, sometimes referred to as a first position, which is in fluid communication with the syringe pump 406 via the syringe hose 407. In the embodiments, the syringe pump 406 pumps solvent for ten seconds at a flow rate of six milliliters per minute to the first sample collection device 100A, which is positioned in the solvent fill position 606. Based on this, it is understood that the system 400 depicted will have eight total pulses of solvent, one for each time a sample collection device 100 is positioned in the solvent fill position 606.

Based on this, the system 400 shown in FIG. 4, upon beginning the analysis process, with all sample collection devices 100 in place and holding their respective samples, the rotary disc 200 begins with a first receptacle (the receptacle 206 counterclockwise to the inlet 902), holding a first sample collection device 100A, as shown in FIG. 6. The first receptacle holds the first sample collection device 100A, which is positioned in the first position 606, i.e. the solvent fill position. The syringe pump 406 is in fluid communication with the solvent fill position 606 and, at the beginning of the process, in fluid communication with the first sample collection device 100A.

A last sample collection device 100N is held in the voltage application position 608, or simply referred to as a second position, and corresponds with a last receptacle in the plurality of receptacles 206. The computer 402 instructs the controller 506 to actuate the electric motor 504 causing it to advance the rotary disc 200 about the central longitudinal axis 208. The advancement positions a next sample collection device at the first position 606. The computer 402 then instructs the syringe pump 406 to pump solvent into the next sample collection device. For reference, in FIG. 6, the next sample collection device is immediately counterclockwise to the first sample collection device 100A.

This advancement also causes the last sample collection device 100N to advance clockwise. It should be noted that, at this point, the last sample collection device 100N has not yet received solvent at the first position 606 and also did not receive high voltage at the second position 608. The computer instructs high voltage application of a sample collection device 100 only after the sample collection device has been in fluid communication, i.e. received solvent at the first position.

The advancement then positions the first sample collection device 100A at the second position 608, i.e. the high voltage application position. The power source is electrically-coupled with the first sample collection device 100A at the second position 608. The computer 402 instructs the mass spectrometer 404 to apply a high voltage from its internal power source to the first sample collection device 100A. The mass spectrometer 404 is always under vacuum and the sampling inlet 902, which is a metal, such as stainless steel, is exposed to the outside atmosphere. The high voltage application causes a voltage difference, sometimes referred to as a voltage differential between the first sample collection device 100A, which is at about four kV to about seven kV, and the sampling inlet 902, which is sometimes grounded and sometimes floated to approximately 100 volts (V) to 200 V. The voltage difference causes the solvent and resulting extracted products and its ions from the solid media containing the analyte to be sprayed into the sampling inlet 902. The vacuum from the mass spectrometer 404 is applied to the distal end 116 of the first sample collection device and assists with collecting the extracted products and its ions, but much less so than the voltage difference. The mass spectrometer 404 then analyzes the resulting extracted products from the first sample collection device 100A. The analysis determines the chemical composition and concentration of the resulting extracted products. It should be noted that the resulting extracted products, most importantly extracted analytes, are in liquid phase as they exit the distal 116 end of the first sample collection device 100A. However, due to the voltage difference, the extracted analytes are gas phase ions by the time they enter the mass spectrometer 404.

Analysis of samples in the system 400 continue by the advancement of the rotary disc 200 based on computer executable instructions stored on the computer 402. Thus, the pumping of solvent by the syringe pump 406 into sample collection devices 100 at the first position 606 continues. The high voltage application at the second position 608 continues for sample collection devices 100 that were previously in the first position 606 and received solvent from the syringe pump 406. The vacuum remains on. Extracted products are sprayed into the sampling inlet 902 and those extracted products are analyzed by the mass spectrometer 404. The process continues until all sample collection devices 100 have had their respective extracted products analyzed by the mass spectrometer 404.

Stated more simply, the process continues in such fashion that the rotary disc 200 continues advancing through all sample collection devices 100 from the first sample collection device 100A to the last sample collection device 100N, until: 1) the last sample collection device 100N has advanced to the first position 606 and received solvent from the syringe pump 606; 2) the last sample collection device 100N has advanced to the second position 608 and received the high voltage application and had its resulting extracted products sprayed into the sampling inlet 902; and 3) the mass spectrometer 404 analyzes the last sample collection device's 100N resulting extracted products.

Data obtained by the analysis can be shown and/or represented to a tangible medium for user verification, such as providing a visual verification to the user which could be useful before taking further action. Examples of the tangible medium include the display screen associated with the computer 402, hard copy printouts of data, as well as other media using the analysis data such as, for example, a computer having computer-readable instructions that is configured to use output from the embodiments.

Although eight sample collection devices 100 are depicted in the system 400, nomenclature for the first and last sample collection devices 100A and 100N is chosen to accommodate any number sample collection devices, hence the use of the "N" designation. The assigned number of N is equal to the number of sample collection devices 100, which is determined by the number of receptacles in the plurality of receptacles 206. Additionally, it is understood that nomenclature can be adapted upon actuation, i.e. rotation, of the rotary disc 200, so that the first sample collection device 100A then moves to the second position 608. The last sample collection device 100N then advances to eventually receiving solvent in the solvent fill position 606 and having high voltage applied in the second position 608.

The syringe pump 406 is configured to pump solvent to the first position 606 and then wait thirty seconds. For the process associated with the system 400 in FIG. 4, the rotary disc 200 rotates 45 degrees. This is based on the rotary disc 200 having eight receptacles 206 and, therefore, eight sample collection devices 100. A person having ordinary skill in the art will recognize, however, that the degrees of rotation can vary based on the diameter of the rotary disc 200, the axial-spacing about the central longitudinal axis 208 of the receptacles 206, and the number of receptacles. In many embodiments, rotation is a range of about 30 degrees to about 90 degrees. Solvent is then pumped to the first position 606 and high voltage is applied at the second position 608 to the proximal end 114. Analysis is performed by the mass spectrometer 404 for thirty seconds. Thus, after rotating, a thirty seconds waiting period is observed before the next rotation. It should be noted that the analysis time can vary, depending on application-specific conditions such as, for example, sample constituents and mass spectrometer type. Likewise, thirty seconds is an example and should not be construed as being limiting. As such, times greater than or less than thirty seconds can be used. The rotary disc 200 then rotates and the process continues until all sample collection devices 100 containing samples have been analyzed and their chemical compositions and concentrations determined.

The electric cable 605 can be referred to as a high voltage cable. The wire 604 can also be referred to as a high voltage wire. Various conductive clips, such as copper, can be used to connect the high voltage cable 605 to the wire 604. As the rotary disc 200 rotates to the next position, the sample collection device 100 that was in front of the inlet 902 comes in contact with the high voltage wire 604 and the high voltage is applied to the proximal end 114. The high voltage can be either positive or negative polarity depending on the analyte of interest, which is sprayed with the solvent into the inlet 902. This creates a Taylor cone. After all samples in the sample collection devices 100 have been analyzed, an analyst simply needs to replace used sample collection devices with new, unused sample collection devices. Should the sampling system 400 be operating continuously, the analyst would change the sample collection devices 100 before the mass spectrometer 404 completes its analysis of the sample in the last sample collection device 100N.

As shown in FIG. 6, the first sample collection device 100A is in a first position 606, which is often referred to as a solvent fill position. The syringe 406 then pumps solvent to the first sample collection device 100A and its associated solid media, i.e. the sample in the first sample collection device 100A. The rotary disc 200 when coupled to the electric motor 504 and controller 506, is configured to advance about the central longitudinal axis 208 upon instructions from the computer 402 sending computer executable instructions to the controller 506 and electric motor 504.

The advancement positions the first sample collection device 100A to the second position 608. The advancement causes the computer 402 to send computer executable instructions to the mass spectrometer 404 to apply a high voltage from the mass spectrometer's power source. The high voltage is applied to the proximal end 114 of the first sample collection device 100A after it advances to the second position 608. The mass spectrometer 404 applies a vacuum at its inlet 902. The amount of vacuum depends on the type of mass spectrometer 404 used and application-specific embodiments. In some embodiments, the high voltage applied is a range of 4 to 5 kV. In other embodiments, the high voltage applied is a range of 4 to 7 kV. While in other embodiments, the high voltage applied is a specific voltage such as, for example, 7 kV. Specific voltage levels and ranges are based on application-specific conditions and, as such, can be greater or less than that above voltage ranges.

FIG. 9 and reference character 900 depict the positioning of the first sample collection device 100A and the rotary disc 200 in relation to the mass spectrometer's inlet 902 after the rotary disc has rotated and placed the first sample collection device at the second position 608. For ease of viewing in FIG. 9, application of the high voltage to the proximal end 114 of the first sample collection device 100A is not shown. Positioning is such that as high voltage is applied, solvent and any resulting extracted products from the solid media sample are pulled through the hole 102 (not visible in the side view of FIG. 9) at the distal end 116 into the inlet 902, so that the mass spectrometer 404 can perform analysis.

Additionally, positioning assures unimpeded motion of the rotary disc 200 and sample collection devices 100 with objects such as, for example the mass spectrometer 404, while still allowing for a Taylor cone into the inlet 902. Appropriate positioning is controlled by the distal end 116 in relation to the inlet 902. In the embodiments, in the second position 608, the distal end 116 is five millimeters vertically (depicted as d1) above and five millimeters horizontally (depicted as d3) from the inlet 902, which is approximately a 45 degree angle. When properly positioned, the second side 802 of the rotary disc 200 is nine millimeters vertically (depicted as d2) above the inlet 902. As shown in FIG. 9, the outer edge 204, the second side 802, and the distal end 116 are unimpeded.

The positioning and spacing dimensions can be varied based on application-specific conditions. For instance, the depth that the sample collection devices 100 sit within the rotary disc 200 can be varied to control ion signal or concentration of analytes reaching the inlet 902. Based on this, the receptacles 206 can be optimized for trace and concentrated analytes by modifying the shape and dimensions of the inner walls 302.

Theory of Operation and Working System

Using the embodiments includes preparing the sample collection devices 100 and inserting the sample collection devices into the receptacles 206. The sample collection devices 100 are filled with the sample, i.e. the solid media and any analyte contained in the solid media. Filling of the sample collection devices 100 can be done either before or after inserting the sample collection devices into the receptacles 206. Solvent is applied to the sample at the first position 606 and voltage is applied at the second position 608. Analysis of the sample is then performed at the second position 608 by the mass spectrometer 404 to determine whether an analyte is present or not present, i.e. whether an analyte is detected or not detected in the sample. When an analyte is detected, the mass spectrometer 404 determines the analyte's chemical composition and concentration.

The rotary disc 200 can move clockwise or counterclockwise, depending on the electric motor 504 configuration and application-specific conditions. For simplicity, however, rotational movement herein is described as clockwise. The rotary disc 200 moves in a clockwise manner, rotating 45 degrees after each sample is analyzed. Computer executable instructions stored on a nontransitory computer readable medium such as, for example, the computer 402, provide instructions for a thirty seconds mass spectrometer 404 analysis time.

The embodiments enable solvent to be applied prior to analysis in the "prep," i.e. the first position 606, and when the sample collection device 100 moves into the "spray," i.e. the second position 608, high voltage is applied to initiate the electrospray. The high voltage line is held above the sample collection device 100 that is aligned with the inlet 902 and makes contact with the proximal end 114 only when in the second position 608. Depending on the mass spectrometer 404, the solvent and the high voltage can either be applied by the mass spectrometer or the external syringe pump 406 and an external power supply (not shown in the figures). The duty cycle of the system 400, via the computer 402 or mass spectrometer 404, can be changed to allow additional extraction time (after solvent deposition) in the sample collection device 100 prior to analysis as needed.

The solvent is applied to the solid media and the high voltage is applied to the proximal end 114 of the sample collection device 100. The solvent extracts the analyte and separates the analyte from the solid media to the solvent within the sample. High voltage is applied to the sample collection device 100 to form a spray plume at the distal end 116 where the hole 102 is located. Voltage is applied based on application-specific conditions, which can be for up to thirty seconds. The analyte is ionized and its chemical composition and concentration are then determined by the mass spectrometer 404.

The solvent extracts the analyte within the solid media sample. Some examples of the solvent include methanol, ethanol, propanol, isopropanol, acetonitrile, water, water mixed with organic solvents, and combinations thereof. The amount of solvent varies depending on the size of the sample collection device 100 and the solid matrix. The amount solvent is directly proportional to the size of the sample collection device 100 (i.e., as the size of the sample collection device increases, so does the amount of solvent used). Similarly, to increase the amount of time a spray plume is being produced, more solvent may be added. In some embodiments, the solvent may be added sequentially (e.g., three 2 milliliters aliquots) or all at once (e.g., one 6 milliliters portion). In other embodiments, the solvent is added in aliquots ranging from about one milliliter to about two milliliters.

In some embodiments, an additive is used in conjunction with the solvent. The additive assists with the extraction of the analyte of the solid media. The additive is added to the solvent prior to adding the solvent to the solid media within the sample collection device to form a mixture of the solvent and additive. Some examples of the additive that may be used with the solvent include acetic acid, formic acid, ammonium acetate, and combinations thereof. The amount of additive differs based on the additive and solvent that is used. For example, a mixture of methanol as the solvent and one percent formic acid as the additive may be used.

Sample analysis includes determining a sample analysis, thereby determining whether an analyte is present in the solid media and, when present, the chemical composition and concentration of the analyte. Additionally, if multiple analytes are detected, the chemical composition and concentration of each analyte is determined. When no analyte is detected, it is reported as no analyte detected or similar designation. Analyte presence, chemical composition, and concentration are determined by analyte standards of the molecule of interest. For example, if the data from the sample matches the standard, the target analyte is present. The mass spectrometer 404 performs the analysis using known techniques. The embodiments result in about sixty samples being examined in the same time as one sample is examined for liquid chromatography mass spectrometry (LC-MS).

After sampling the sample in a sample collection device 100, the rotary disc 200 advances to the next position where the used sample collection device is removed and a new sample collection device is now aligned with the inlet 902. The new sample collection device 100, i.e. solvent has been applied to the first sample collection device 100A, which is now in the second position 608 and in contact with the wire 604 providing high voltage, which initiates an electrospray (the Taylor cone) into the inlet 902 for sample analysis. Rotation occurs and the next sample collection device 100 is moved into the first position 606, i.e. the "prep" position and has solvent applied. Rotation is continuous and customizable to the number of samples needing analysis. The sample collection devices 100 that have already been analyzed do not need to be removed right away but should be replaced if the system 400 is set to continuously sample. For the system 400 shown in FIG. 4, eight sample collection devices 100 are used, which means that the sample collection devices would need to be replaced at least every six analyses to ensure no repetitive analyses. Increasing the diameter of the rotary disc 200 and ultimately the number of receptacles 206 can add to the amount of samples run during each cycle and increase the time in between sample removal and loading.

Rotation of the rotary disc 200 can be controlled by a timer and be on a continuous loop based on instruction from the computer 402, or be triggered by a contact closure signal from the mass spectrometer 404. Similarly, once positioned the start-up of the sequence of solvent and high voltage application can be controlled by the computer 402 using a timer or be triggered by a contact closure signal from the mass spectrometer 404.

In some embodiments, the sample collection device 100 may be cleaned and reused in the field or at the laboratory to obtain another solid media sample. In other embodiments, the sample collection device 100 is discarded after sample collection. When the sample collection device 100 is cleaned and reused, the solid media is removed from the sample collection device and the sample collection device is submerged and sonicated in a solvent. The submerging and sonication step is repeated until the sample collection device 100 is cleaned (i.e., a clean standard sample is run with the sample collection device 100, which shows no chemicals present). In some examples, different solvents are used to clean the sample collection device 100 each time the sample collection device 100 is submerged and sonicated.

While the embodiments have been described, disclosed, illustrated and shown in various terms of certain embodiments or modifications which it has presumed in practice, the scope is not intended to be, nor should it be deemed to be, limited thereby and such other modifications or embodiments as may be suggested by the teachings herein are particularly reserved especially as they fall within the breadth and scope of the claims here appended.

What is claimed is:

1. A sample collection apparatus, comprising:
   a platform having a first side, a second side, and an outer edge; and
   a plurality of receptacles extending through said platform from said first side to said second side, wherein each receptacle in said plurality of receptacles is configured to removably-hold a sample collection device, said sample collection device, comprising:
      a proximal end and a distal end, said distal end having a hole;
      wherein said sample collection device is constructed of a conductive polymer, said conductive polymer including a mixture of carbon nanotubes and a polymer.

2. The apparatus according to claim 1, wherein said platform is a disc.

3. The apparatus according to claim 1, wherein said platform is rectangular.

4. The apparatus according to claim 1, wherein each receptacle in said plurality of receptacles is an aperture through said platform.

5. The apparatus according to claim 1, wherein said plurality of receptacles is a range of about four to about twelve receptacles.

6. The apparatus according to claim 1, wherein said sample collection device is a multi-faced pyramid.

7. The apparatus according to claim 1, wherein said sample collection device is a cylindrical cone.

8. The apparatus according to claim 1, wherein said polymer is selected from the group consisting of polyethylene terephthalate, acrylonitrile butadiene styrene, polylactic acid, polyetherketoneketone, polyether ether ketone, polycarbonate, polyphenylene sulfide, polyvinylidene fluoride, and combinations thereof.

9. The apparatus according to claim 1, wherein said platform is constructed of a non-conductive, chemically-inert plastic.

10. The apparatus according to claim 1, said platform having a central longitudinal axis, wherein said plurality of receptacles are axially-spaced at equal distance about said central longitudinal axis.

11. The apparatus according to claim 10, wherein said spacing of said plurality of receptacles is a range of about 30 degrees to about 90 degrees.

12. The apparatus according to claim 1, wherein said sample collection device is configured to hold a solid media containing an analyte.

13. The apparatus according to claim 12, wherein said solid media is selected from the group consisting of soil, sand, sediment, waste, pure analytes, and combinations thereof.

14. The apparatus according to claim 12, wherein said analyte is selected from the group consisting of perfluoroalkyl substances, polyfluoroalkyl substances, energetics, chemical warfare agent simulants, drugs of abuse, pesticides, and combinations thereof.

* * * * *